United States Patent
Schaffer et al.

(10) Patent No.: US 11,957,604 B2
(45) Date of Patent: *Apr. 16, 2024

(54) VARYING DENSITY OF A MODEL FOR MANUFACTURING A LINER

(71) Applicant: Precision Valve & Automation, Inc., Halfmoon, NY (US)

(72) Inventors: Karin Cecilia Backlin Schaffer, Loudonville, NY (US); Jeffrey L. Erenstone, Lake Placid, NY (US)

(73) Assignee: PRECISION VALVE & AUTOMATION, INC., Halfmoon, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/147,562

(22) Filed: Jan. 13, 2021

(65) Prior Publication Data

US 2021/0137705 A1    May 13, 2021

Related U.S. Application Data

(63) Continuation of application No. 15/444,841, filed on Feb. 28, 2017, now Pat. No. 10,905,568.

(Continued)

(51) Int. Cl.
*A61F 2/50* (2006.01)
*A61F 2/78* (2006.01)
(Continued)

(52) U.S. Cl.
CPC .............. *A61F 2/5046* (2013.01); *A61F 2/80* (2013.01); *B29C 64/386* (2017.08); *B33Y 10/00* (2014.12);
(Continued)

(58) Field of Classification Search
CPC ........ A61F 2/5046; A61F 2/80; A61F 2/7812; A61F 2/78; A61F 2002/5047; A61F 2002/5053; A61F 2002/5049; A61F 2/5044; A61F 2002/7837; A61F 2002/802; A61F 2007/0051; A61F 2002/762;
(Continued)

(56) References Cited

U.S. PATENT DOCUMENTS

| 4,923,475 A | 5/1990 | Gosthnian et al. |
| 5,050,090 A | 9/1991 | Golub et al. |

(Continued)

OTHER PUBLICATIONS

U.S. Appl. No. 15/444,841, filed Feb. 28, 2017; Gau 2118; Confirmation No. 7069; Customer No. 05409.

(Continued)

*Primary Examiner* — Darrin D Dunn
(74) *Attorney, Agent, or Firm* — Schmeiser, Olsen & Watts, LLP

(57) ABSTRACT

A system and method for method including receiving data representing coordinates of a shape of a body part, forming a model of a flexible inner liner based upon the received data, the flexible inner liner configured to be placed over the body part, receiving, as input, a thickness and an offset of the model of the flexible inner liner, assigning a default density to an internal structure of the model; and varying the default density of the model without changing an outer geometry of the model to create a modified model of the flexible inner liner.

12 Claims, 8 Drawing Sheets

Related U.S. Application Data

(60) Provisional application No. 62/301,363, filed on Feb. 29, 2016.

(51) Int. Cl.
*A61F 2/80* (2006.01)
*B29C 64/386* (2017.01)
*B33Y 10/00* (2015.01)
*B33Y 50/00* (2015.01)
*B33Y 50/02* (2015.01)
*B33Y 80/00* (2015.01)
*G05B 19/4099* (2006.01)
*B29L 31/00* (2006.01)

(52) U.S. Cl.
CPC .............. *B33Y 50/00* (2014.12); *B33Y 50/02* (2014.12); *B33Y 80/00* (2014.12); *A61F 2002/5049* (2013.01); *A61F 2002/505* (2013.01); *A61F 2002/5053* (2013.01); *A61F 2002/5056* (2013.01); *A61F 2/7812* (2013.01); *B29L 2031/7532* (2013.01); *G05B 19/4099* (2013.01); *G05B 2219/35134* (2013.01); *G05B 2219/49007* (2013.01)

(58) Field of Classification Search
CPC ...... A61F 2002/7635; A61F 2002/7806; A61F 2002/7875; G06F 30/00; G06F 30/20; G06F 30/23; B33Y 80/00; B33Y 50/00; A42B 3/064; A42B 3/125; A42B 3/124; G01B 5/008; G06T 19/00
See application file for complete search history.

(56) References Cited

U.S. PATENT DOCUMENTS

| | | | |
|---|---|---|---|
| 5,444,881 A | 8/1995 | Landi et al. | |
| 5,496,610 A | 3/1996 | Landi et al. | |
| 5,522,402 A | 6/1996 | Cooley | |
| 5,539,649 A | 7/1996 | Walsh et al. | |
| 5,552,992 A | 9/1996 | Hunter | |
| 6,068,659 A | 5/2000 | O'Brien, Jr. | |
| 6,136,039 A | 10/2000 | Kristinsson et al. | |
| 6,177,034 B1 | 1/2001 | Ferrone | |
| 7,162,322 B2 | 1/2007 | Arbogast et al. | |
| 7,611,476 B2 | 11/2009 | Taranow | |
| 7,937,973 B2 | 5/2011 | Sorensen et al. | |
| 8,005,651 B2* | 8/2011 | Summit | A61F 5/022 703/1 |
| 8,173,268 B2 | 5/2012 | Maus et al. | |
| 8,175,734 B2* | 5/2012 | Fogel | G06T 19/00 700/98 |
| 8,366,789 B2 | 2/2013 | Summit | |
| 8,423,167 B2* | 4/2013 | Sanders | G06F 30/00 700/118 |
| 8,449,707 B2* | 5/2013 | Simmons | B32B 3/28 156/219 |
| 8,523,951 B2* | 9/2013 | Kania | A61F 2/7812 623/36 |
| 8,551,184 B1* | 10/2013 | Herr | A61F 2/6607 623/47 |
| 9,072,463 B2 | 7/2015 | Sanders et al. | |
| 9,265,629 B2* | 2/2016 | Kelley | A61F 2/7812 |
| 9,283,660 B1 | 3/2016 | Dignam et al. | |
| 9,469,075 B2 | 10/2016 | Zachariasen et al. | |
| 9,480,581 B2 | 11/2016 | Layman et al. | |
| 9,545,127 B1* | 1/2017 | Sandifer | A42B 3/121 |
| 9,636,238 B2 | 5/2017 | Sanders et al. | |
| 9,782,274 B2 | 10/2017 | Summit et al. | |
| 10,639,173 B2* | 5/2020 | Walter | A61F 2/7812 |
| 10,980,306 B2* | 4/2021 | Weber | A42B 3/125 |
| 2004/0068337 A1 | 4/2004 | Watson et al. | |
| 2004/0260402 A1* | 12/2004 | Baldini | A61F 2/5046 623/36 |
| 2005/0145563 A1 | 7/2005 | Boyd et al. | |
| 2006/0020348 A1 | 1/2006 | Slemker et al. | |
| 2006/0105135 A1 | 5/2006 | Chien et al. | |
| 2006/0111792 A1* | 5/2006 | Shannon | A61F 2/7812 623/36 |
| 2006/0123542 A1 | 6/2006 | Wilson et al. | |
| 2007/0080479 A1* | 4/2007 | Arbogast | A61F 2/5046 264/222 |
| 2007/0162153 A1* | 7/2007 | Barnes | A61F 2/5046 623/36 |
| 2008/0155735 A1 | 7/2008 | Ferrara | |
| 2008/0161963 A1 | 7/2008 | Slemker et al. | |
| 2008/0188948 A1* | 8/2008 | Flatt | A61F 2/5046 264/222 |
| 2010/0023149 A1* | 1/2010 | Sanders | G06F 30/00 700/98 |
| 2010/0030083 A1* | 2/2010 | Sanders | A61B 5/447 600/474 |
| 2010/0161076 A1* | 6/2010 | Pallari | A43B 13/183 700/98 |
| 2011/0004335 A1 | 1/2011 | Summit et al. | |
| 2011/0082578 A1* | 4/2011 | Stanhope | G06T 19/00 700/98 |
| 2011/0126973 A1 | 6/2011 | Andrewlavage, Jr. et al. | |
| 2011/0241240 A1 | 10/2011 | Gothait et al. | |
| 2012/0022657 A1 | 1/2012 | Iannotti et al. | |
| 2012/0116539 A1 | 5/2012 | Armstrong et al. | |
| 2012/0143077 A1 | 6/2012 | Sanders et al. | |
| 2012/0173001 A1* | 7/2012 | Caspers | A61F 2/80 623/34 |
| 2013/0035770 A1* | 2/2013 | Egilsson | A61L 27/56 623/36 |
| 2013/0052398 A1 | 2/2013 | Dean et al. | |
| 2013/0124151 A1 | 5/2013 | Mech et al. | |
| 2013/0150981 A1 | 6/2013 | Summit | |
| 2013/0226533 A1 | 8/2013 | Summit et al. | |
| 2013/0282141 A1* | 10/2013 | Herr | A61F 2/5046 700/98 |
| 2014/0005800 A1* | 1/2014 | Kelley | A61F 2/7812 623/36 |
| 2014/0088929 A1 | 3/2014 | Suttin, Sr. et al. | |
| 2014/0149082 A1* | 5/2014 | Sanders | A61F 2/5046 703/1 |
| 2014/0163697 A1 | 6/2014 | Sanders et al. | |
| 2014/0173812 A1* | 6/2014 | Krueger | A41D 13/0155 2/455 |
| 2014/0188260 A1 | 7/2014 | Layman et al. | |
| 2014/0228860 A1 | 8/2014 | Steines et al. | |
| 2014/0288670 A1 | 9/2014 | Phillips | |
| 2014/0303748 A1* | 10/2014 | Armstrong | A61F 2/5046 623/36 |
| 2014/0316526 A1 | 10/2014 | Grotz | |
| 2015/0142150 A1 | 5/2015 | Layman et al. | |
| 2015/0278414 A1 | 10/2015 | Zhou et al. | |
| 2015/0297369 A1 | 10/2015 | Mosler et al. | |
| 2015/0328840 A1 | 11/2015 | Zachariasen et al. | |
| 2015/0359644 A1 | 12/2015 | Sanders et al. | |
| 2016/0005851 A1 | 3/2016 | Song | |
| 2016/0331563 A1 | 11/2016 | Kane et al. | |
| 2017/0131788 A1* | 5/2017 | Kaku | G06F 3/018 |
| 2017/0161405 A1 | 6/2017 | Ishizuka et al. | |
| 2017/0174346 A1 | 6/2017 | Wilson et al. | |
| 2017/0216056 A1* | 8/2017 | Hill | A41D 27/06 |
| 2017/0231788 A1* | 8/2017 | Kelley | A61F 7/02 623/37 |
| 2017/0246013 A1 | 8/2017 | Erenstone | |
| 2017/0290685 A1 | 10/2017 | Montez et al. | |
| 2017/0323037 A1 | 11/2017 | Schroeder | |
| 2017/0354367 A1* | 12/2017 | Laghi | A61B 5/6811 |
| 2017/0360578 A1 | 12/2017 | Shin et al. | |
| 2018/0098865 A1 | 4/2018 | Mojica et al. | |
| 2018/0235779 A1 | 8/2018 | Dudding | |
| 2018/0243111 A1 | 8/2018 | Hand | |
| 2018/0243112 A1 | 8/2018 | Hand | |
| 2019/0021880 A1* | 1/2019 | Herr | G06F 30/23 |

(56) References Cited

U.S. PATENT DOCUMENTS

2021/0022891 A1*  1/2021  Herr .......................... A61F 2/78
2022/0133173 A1*  5/2022  Herr ..................... A61F 2/5044
                                                                600/438
2022/0211522 A1*  7/2022  Polta .................... A61F 2/5044

OTHER PUBLICATIONS

Office Action (dated Nov. 19, 2018) for U.S. Appl. No. 15/444,841, filed Feb. 28, 2017.
Final Office Action (dated Jul. 29, 2019) for U.S. Appl. No. 15/444,841, filed Feb. 28, 2017.
Office Action (dated Apr. 16, 2020) for U.S. Appl. No. 15/444,841, filed Feb. 28, 2017.
Notice of Allowance (dated Sep. 28, 2020) for U.S. Appl. No. 15/444,841, filed Feb. 28, 2017.
PCT International Search Report Form PCT/ISA/220, International Application No. PCT/US/2017/019878, International Filing Date: Feb. 18, 2017, mailing date of Search Report: dated Jun. 5, 2017.

\* cited by examiner

VARYING DENSITY OF A MODEL FOR MANUFACTURING A LINER

CROSS-REFERENCE TO RELATED APPLICATIONS

The present application claims priority to U.S. Nonprovisional application Ser. No. 15/444,841, filed on Feb. 28, 2017, and entitled "Prosthetic Limb Socket With Variable Hardness," which claims the benefit of and priority to U.S. Provisional Application No. 62/301,363, filed on Feb. 29, 2016, the entire contents of which are incorporated by reference.

BACKGROUND OF THE INVENTION

1. Field of the Invention

The present invention relates to artificial limb sockets and, more specifically, to a system and method for creating sockets with variable hardness for an improved custom fit.

2. Description of the Related Art

The major component of the interface between the residual (remaining) limb of an amputee and their prosthetic device is called the socket. The socket bears the weight of the body of the user and distributes the load across the prosthesis. Because the shape and structure of each residual limb varies between patients, every socket must be custom made by a certified and licensed practitioner so that it properly fits a patient. Despite the customization of sockets by professionals, traditional prosthetic socket manufacturing does not always allow for the proper distribution of pressure between the residual limb and the prosthetic device. As a result, a poorly designed socket does not distribute pressure properly and will often cause pain or injuries. Additionally, current methods of manufacturing prosthetics are expensive and labor intensive. Accordingly, there is a need in the art for a system and method of designing and manufacturing prosthetic device sockets that improve the fit of the socket while reducing the time and expense associated with manufacturing the improved socket.

BRIEF SUMMARY OF THE INVENTION

The present invention comprises a system and method of producing a prosthetic limb socket using computer-aided design (CAD), computer-aided engineering (CAE), and computer assisted manufacturing (CAM) so that prosthetic practitioners (prosthetists) can design and manufacture custom flexible inner prosthetic supports that better interface with individual amputees and more evenly distribute pressure. More specifically, a system for producing a prosthetic socket according to the present invention includes a data acquisition module configured to form a digital representation of a residual limb from an input of patient data, a computer design module configured to create a digital model of a prosthetic socket having an internal structure based on the digital representation of the residual limb and to allow a user to modify the digital model to adjust the internal structure to change at least a portion of the internal structure of the digital model, and print conversion module associated with the computer design module that is configured to receive the modified digital model from the computer design module and convert the modified digital model into instructions for a manufacturing device. The invention may further comprise a manufacturing device, such as computer-assisted manufacturing machine, that is associated with the print conversion module for receiving the converted modified digital model and for forming a prosthetic socket that corresponds to the modified digital model. The data acquisition module may be configured to receive the input of patient data from a three-dimensional scanner used to take a three-dimensional scan of the residual limb or a three-dimensional scan of a cast of the residual limb. The data acquisition module may also be configured to receive the input of patient data from a practitioner that has measured the residual limb. The computer design module may comprise computer aided design software, and the computer design module may be G-code software.

The present invention also includes a method of producing a prosthetic socket, comprising the steps of acquiring data representing coordinates of a residual limb, forming a digital representation of the residual limb based on the acquired data, creating a digital model of a prosthetic socket having in internal structure based on the digital representation of the residual limb, allowing modifications to the digital model to adjust the internal structure to change at least a portion of the internal structure of the digital model, and converting the modified digital model into instructions for a manufacturing device. The method may additionally include the step of forming an actual prosthetic socket that corresponds to the modified digital model.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
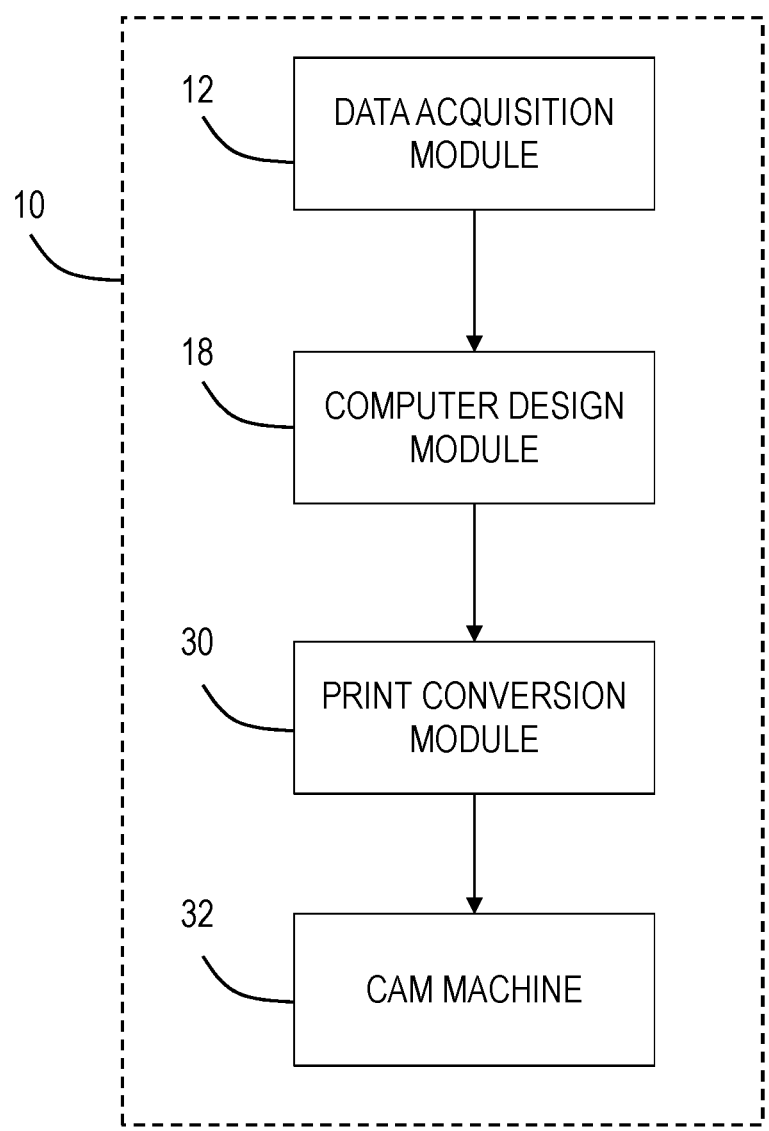
FIG. 1 is a schematic of a system for designing and producing an improved prosthetic socket according to the present invention.
Figure 2:
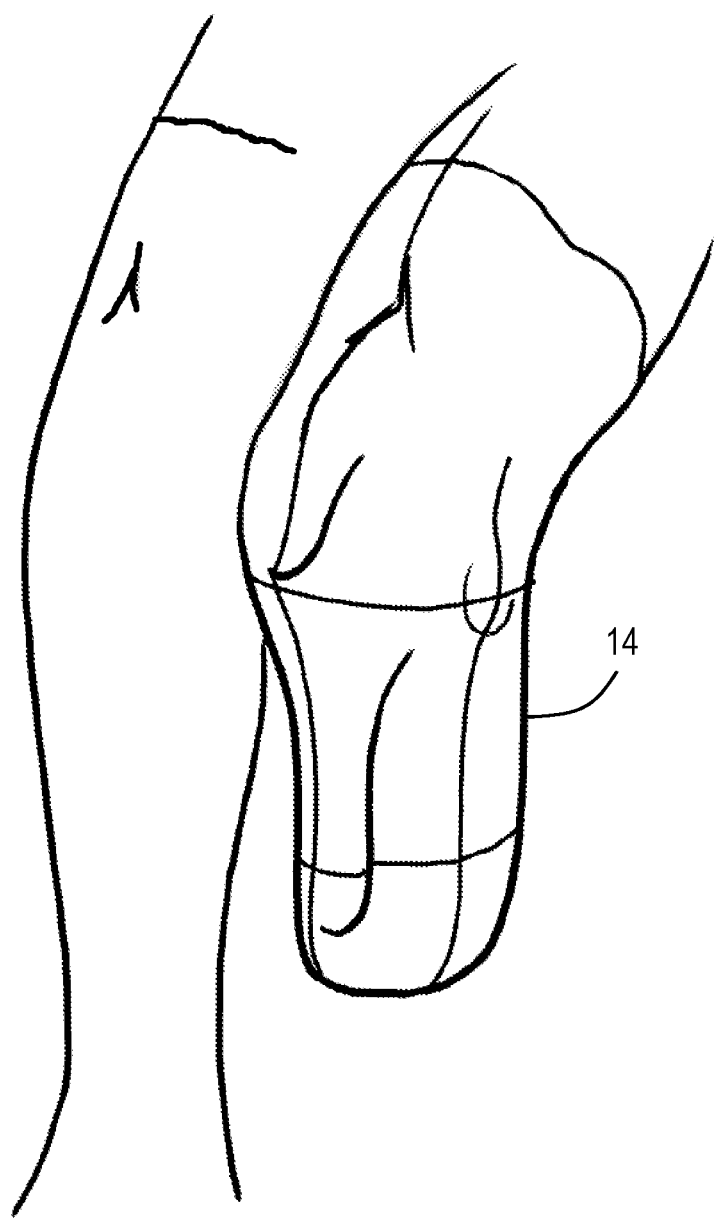
FIG. 2 is a perspective view of a patient residual limb according to the present invention

Referring to the figures, wherein like numerals refer to like parts throughout, there is seen in FIG. 1, a prosthetic socket design system 10 comprising a patient data acquisition module 12 that is configured to acquire the specific anthropomorphic data of a patient having a residual limb 14 to be outfitted with a prosthetic device, as seen in FIG. 2.

Figure 3:
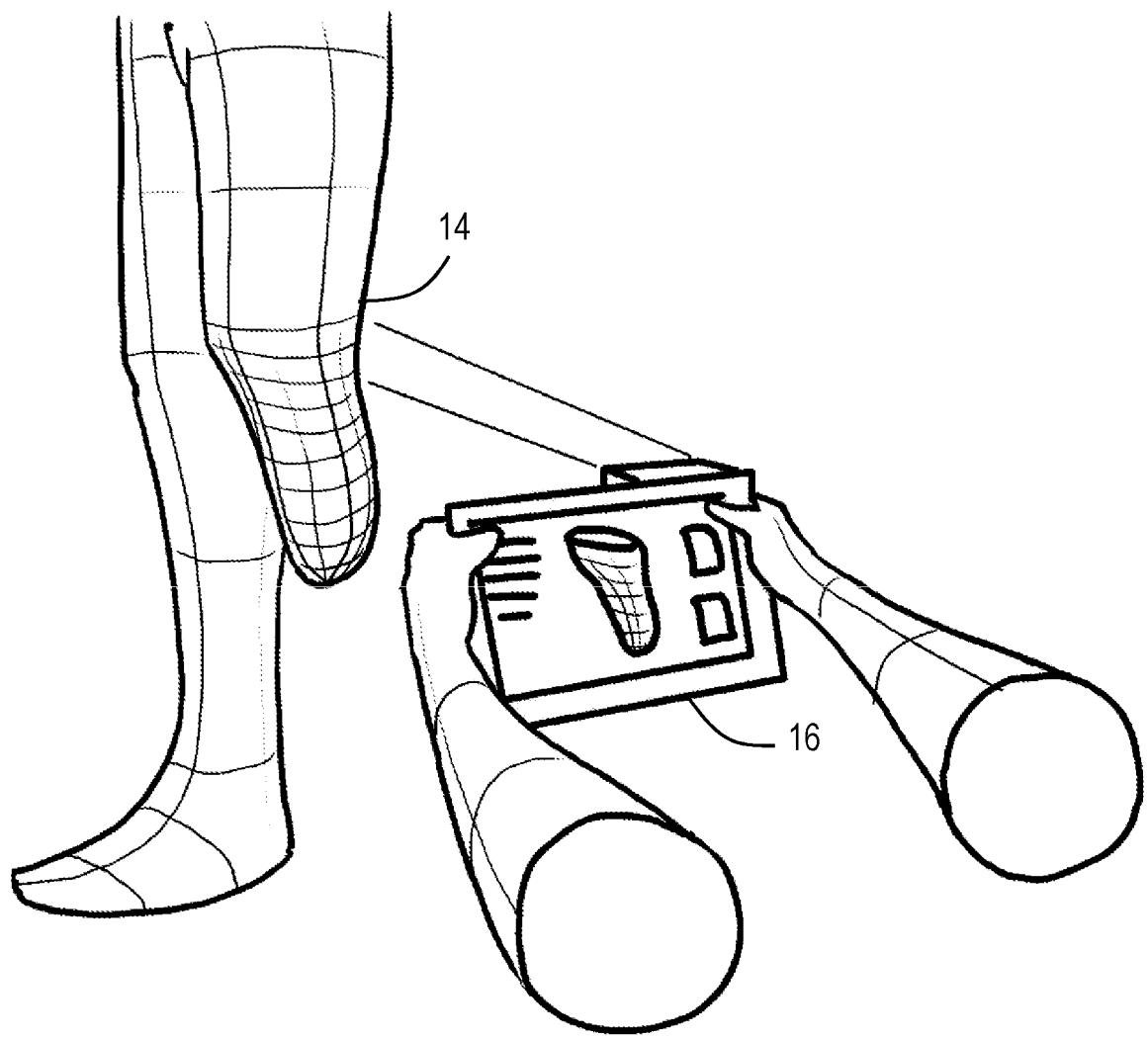
FIG. 3 is a perspective view of the collection of patient residual limb data using a three-dimensional scanner according to the present invention.

Data acquisition module 12 may comprise a digital scanner 16 that acquires patient anthropomorphic data via 3D digital scanning that acquires the coordinates of the bones, fatty tissues, and muscles of the residual limb to be outfitted with the socket and prosthetic device, as seen in FIG. 3. Data acquisition module 12 is configured to digitize the coordinates into a shapefile (digital mold) through use of conventional scanning software. Data acquisition module 12 may alternatively or additionally be configured to acquire patient anthropomorphic data through the digitization of a physical mold. For example, a user may acquire the exact coordinates of a residual limb from a plaster cast of that residual limb using the same 3D scanning process described above and then digitize those coordinates into a shapefile. Data acquisition module 12 may alternatively or additionally be configured to acquire patient anthropomorphic data that is obtained by a user manually measuring predetermined set of coordinates and then entering the coordinates into data acquisition module 12 so that the digital shapefile can be generated.

Figure 4:
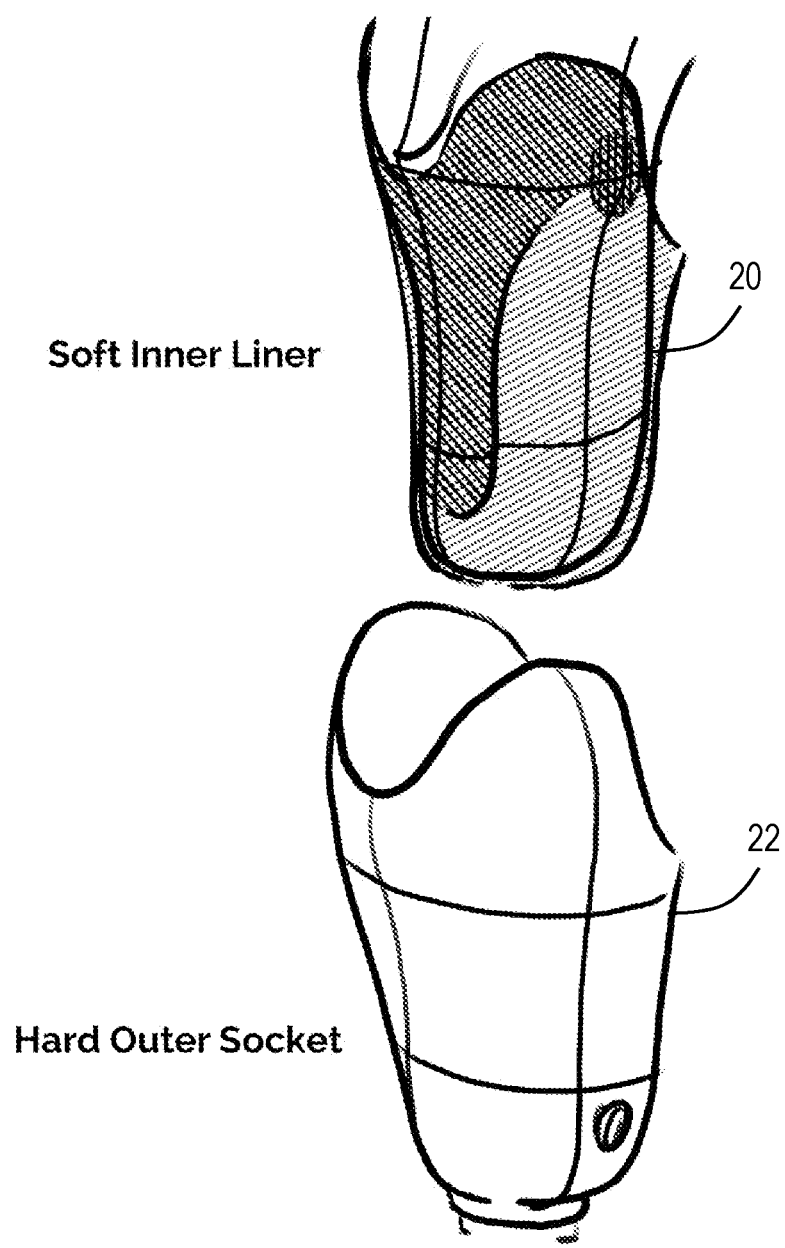
FIG. 4 is perspective view of a prosthetic device having an inner socket modified according to the present invention.
Figure 5:
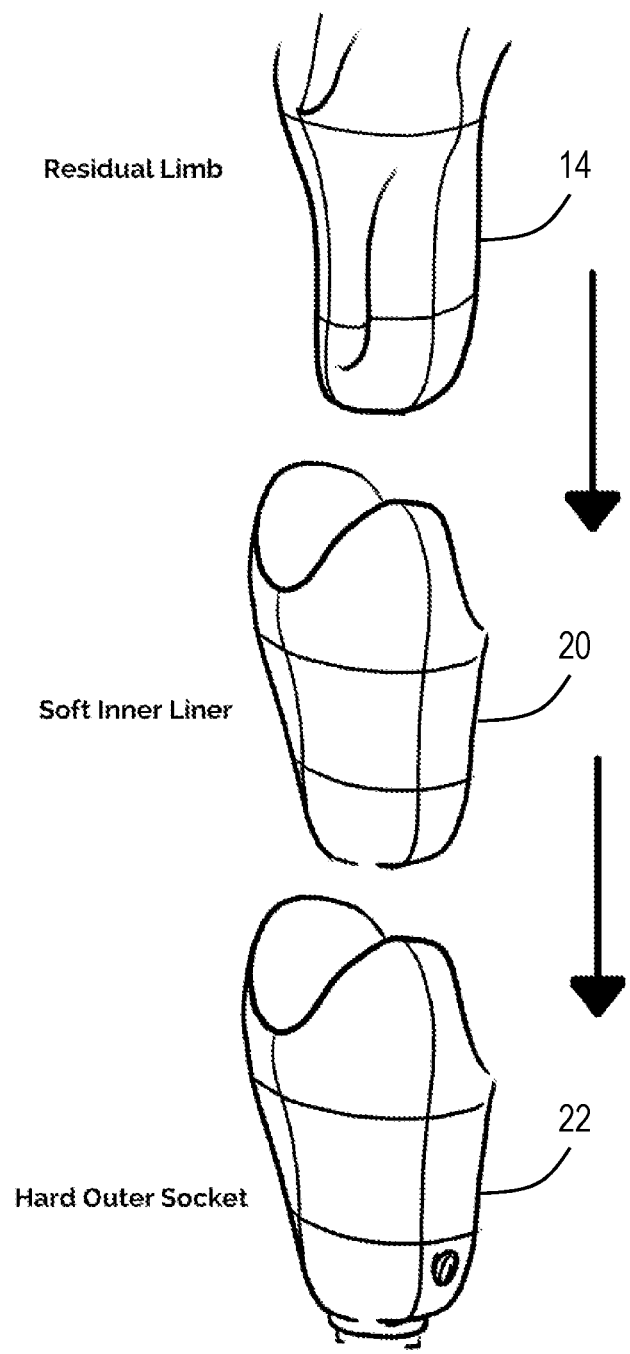
FIG. 5 is a schematic of the attachment of an outer and inner socket to a patient limb according to the present invention.
Figure 6:
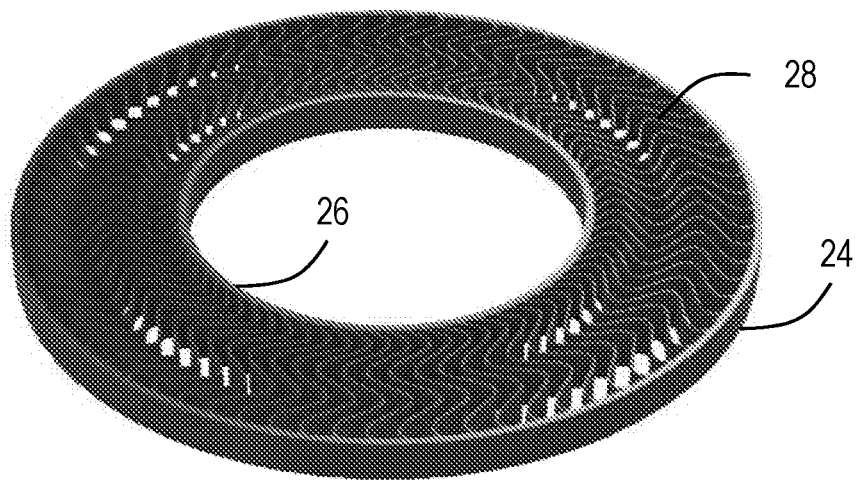
FIG. 6 is a perspective view of a cross-section of an inner socket according to the present invention.
Figure 7:
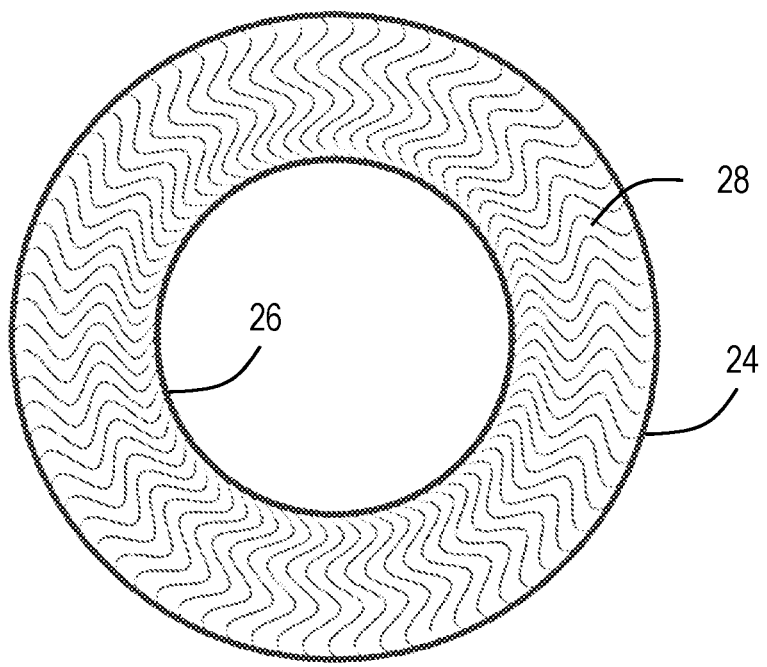
FIG. 7 is a cross-sectional view of an inner socket according to the present invention.

System 10 further comprises a computer design module 18 interconnected to data acquisition module 12 and configured to receive the shapefile once is has been generated. Computer design module 18 may comprise CAD/CAE software that is configured for the present invention. More specifically, computer design module 18 is programmed to display the shapefile for the practitioner and allow the practitioner to enter a desired offset (distance between the residual limb and flexible inner socket) and thickness defining a flexible inner socket 20 as seen in FIG. 4. Inner socket 20 is used as a liner between limb 14 and the hard outer socket 22 of a prosthetic when attaching to limb 14 as seen in FIG. 5. Based upon the user selected offset and thickness, computer design module 18 generates a digital representation of a model socket that can be further manipulated by the practitioner as described herein. Computer design module 18 preferably assigns a default uniform density to the internal structure of the digital socket (the flexible internal supports of the socket) that may then be manipulated by the practitioner. Computer design module 18 is further configured to allow the practitioner to assign areas of the digital socket for increased density of the internal architecture structure. Areas with higher density are used to reduce pressure points that form proximately to any sensitive areas of a residual limb that require lower density areas. Practitioners use their training, expertise, and experience to identify areas on each residual limb that require different levels of density and then use computer design module 18 to make these customized changes to the digital socket and thus the digital shapefile. Referring to FIGS. 6 and 7, an exemplary inner socket 20 according to the present invention may have an outer surface 24 and an inner surface 26 spaced apart by internal structural elements 28, all of which are formed from a single material, such as a polymer or plastic. The number of structural elements 28 may thus be varied to change the flexibility of inner socket 20 while maintaining the same outer geometry. While socket 20 is shown with sinusoidal or triangular wave element (zigzag) structural elements 28, it should be recognized that other shapes may be used if they provide structural stability between outer surface 24 and inner surface 26 and are able to be provided in various densities or amounts.

System 10 further comprises a print conversion module 30 interconnected to computer design module 18 and configured to receive the customized digital shape file. Print conversion module 30 is programmed to convert the digital shapefile into an appropriate file format for computer-assisted manufacturing or three-dimensional (3D) printing. For example, print conversion module 30 may be programmed to convert digital shape file into G-code, a conventional language used to determine the optimal settings of a computer-assisted manufacturing (CAM) machine (or 3D printer). The printing file format, such G-code, is used to determine the extrusion material temperature of the particular machine, the extrusion rate/speed, the build plate temperature, and the tool path (movement of the extruder to form the shape and internal architecture structure of the socket). Print conversion module 30 thus translates the customized shapefile into the corresponding instructions for manufacturing a socket based on the customized shapefile. This process is frequently referred to as slicing and involves the translation of 3D models into instructions that a 3D printer can understand and can be optimized to the particular 3D printer to be used.

Figure 8:
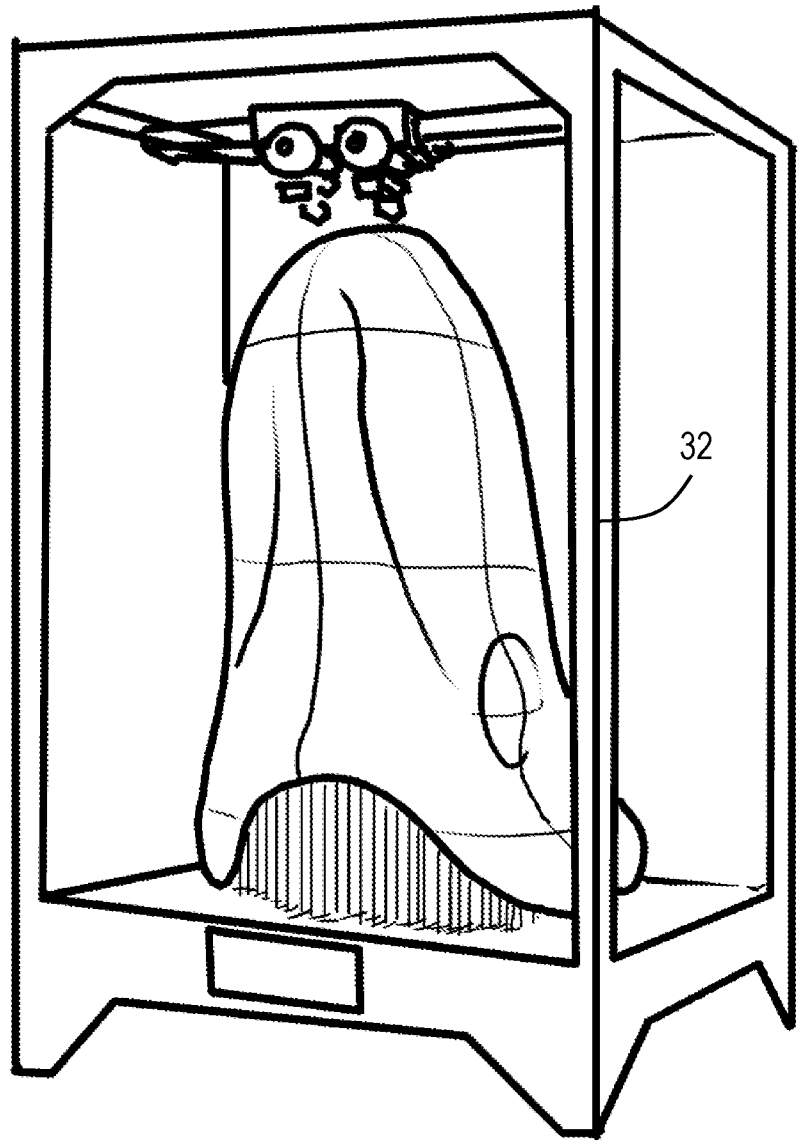
FIG. 8 is a perspective view of a computer-assisted manufacturing machine (3D printer) making an inner socket according to the present invention.

System 10 additionally comprises a CAM machine 32 associated with print conversion module 30 that is configured to manufacture a socket based on the customized shapefile that has been converted into the appropriate language for CAM machine 32 by conversion module 30. For example, CAM machine 32 may use the G-Code produced by print conversion module 30 to fabricate a flexible inner socket as designed by the practitioner using computer design module 18. CAM machine 32 thus uses the G-code specifications and tool paths to physically fabricate an inner socket 20, as seen in FIG. 8. As an example, the Raise3D N2 Plus printer available from Raise3D, Inc. of Santa Clara, California may be used as CAM machine 32.

System 10 may thus be used to produce an artificial limb inner socket that is digitally designed to vary the forces applied to the residual limb for pressure-sensitive and tolerant areas. Moreover, system 10 can produce an inner socket from a single material while maintaining a uniform thickness within the socket yet having variable durometers to address pressure-sensitive and tolerant areas. System 10 makes it easy to control, adjust, and modulate socket pressures and, at the same time, does not require any increased volume of the inner socket, increased weight of the socket, or the use of multiple materials. While system 10 is best used for inner socket design and manufacturing, system 10 could be used for outer socket 22 design as well as for any other medical device or prosthetic element that would benefit from a customized patient fit.

Figure 9:
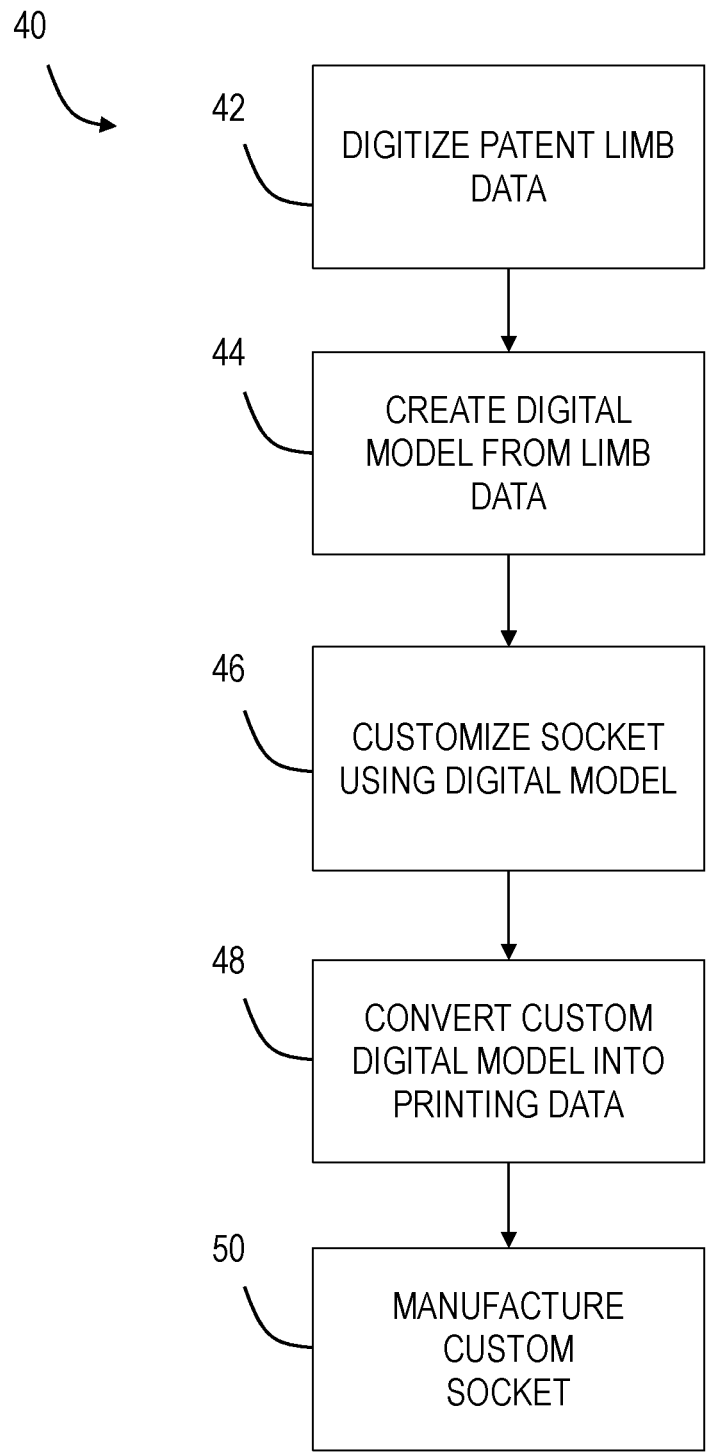
FIG. 9 is a flowchart of a process for designing and producing an improved prosthetic socket according to the present invention.

Referring to FIG. 9, a prosthetic socket manufacturing process 40 according to the present invention begins with the step of digitizing the specific anthropomorphic data of the residual limb of a patient 42. The three preferred approaches of performing this step are digitally scanning the residual limb, digitally scanning a physical cast of the limb, or manually measuring the residual limb and entering the measurements. Next, the scanned data is used to create a digital model 44. Conventional software can be used to develop the digital model, including directly from a 3D/structural scanner if used in step 42. Once the digital model is created 44, a qualified user may then use CAD or computer-aided engineering (CAE) software to develop a customized socket from the digital model 46. As discussed above, this step involves the generation of a default model socket and then adjustment of that model based upon practitioner inputs to develop an ideal internal architecture structure that has variable internal density and thus flexibility to correspond to a particular residual limb. Once the digital model has been customized at step 46, the customized digital model is converted into an appropriate language or protocol for manufacturing by a 3D printer or CAM machine 48. As described above, an acceptable conventional language is G-code and accounts for the particular machine/filament combination, ideal extrusion temperature, extrusion rate/speed, build plate temperature, and tool path of the CAM machine. It should be recognized that the present invention may be used for various types of orthoses, braces, furniture, and protective clothing. Finally, the custom socket is manufactured by CAM machine 50.

As described above, the present invention may be a system, a method, and/or a computer program associated therewith and is described herein with reference to flowcharts and block diagrams of methods and systems. The flowchart and block diagrams illustrate the architecture, functionality, and operation of possible implementations of systems, methods, and computer programs of the present invention. It should be understood that each block of the flowcharts and block diagrams can be implemented by computer readable program instructions in software, firmware, or dedicated analog or digital circuits. These computer readable program instructions may be implemented on the processor of a general purpose computer, a special purpose computer, or other programmable data processing apparatus to produce a machine that implements a part or all of any of the blocks in the flowcharts and block diagrams. Each block in the flowchart or block diagrams may represent a module, segment, or portion of instructions, which comprises one or more executable instructions for implementing the specified logical functions. It should also be noted that each block of the block diagrams and flowchart illustrations, or combinations of blocks in the block diagrams and flowcharts, can be implemented by special purpose hardware-based systems that perform the specified functions or acts or carry out combinations of special purpose hardware and computer instructions.

The invention claimed is:

1. A method comprising:
    receiving data representing coordinates of a shape of a body part;
    forming a model of a flexible inner liner based upon the received data, the flexible inner liner configured to be placed over the body part;
    receiving, as input, a thickness and an offset of the model of the flexible inner liner;
    assigning a default uniform density to an internal structure of the model;
    varying the default uniform density of the model in at least one area of the model without changing the thickness of the model to create a modified model of the flexible inner liner having a non-uniform density, the thickness defined by a distance between an outer surface and an inner surface of the model, wherein the at least one area of the model has a density that different than a density of a remaining area of the model, and a structural configuration of the at least one area of the model includes a plurality of repeating structural elements that are spaced apart from each other by a distance, each repeating structural element extending from the inner surface to the outer surface of the model; and
    converting the modified model into machine readable instructions based on a language for manufacturing the flexible inner line by a 3D printer.

2. The method of claim 1, wherein the flexible inner liner is disposed between the body part and a hard outer layer.

3. The method of claim 1, wherein the distance between the outer surface and the inner surface is unchanged as a function of the default density being varied.

4. The method of claim 1, wherein the structural configuration is modified as a function of the varying.

5. The method of claim 4, wherein the structural configuration is modified by varying a number of the plurality of repeating structural elements extending between the inner surface and the outer surface of the flexible inner liner.

6. The method of claim 1, wherein the plurality of repeating structural elements are one of sinusoidal wave elements and triangular wave elements.

7. The method of claim 1, wherein a material of the model is not varied as a function of the varying.

8. The method of claim 1, wherein the data representing coordinates of the shape of the body part is at least one of: received from a scanner that is configured to scan at least one of the body part and a physical mold of the body part, and received as input from a user that manually measures the body part or the physical mold.

9. The method of claim 1, further comprising: controlling the 3D printer with the machine readable instructions to manufacture the flexible inner liner.

10. A computing system comprising:
    a processor configured to:
        receive data representing coordinates of a shape of a body part;
        form a model of a flexible inner liner based upon the received data, the flexible inner liner configured to be placed over the body part;
        receive, as input, a thickness and an offset of the model of the flexible inner liner;
        assign a default density to an internal structure of the model;
        vary the default uniform density of the model in at least one area of the model without changing the thickness of the model to create a modified model of the flexible inner liner having a non-uniform density, the thickness defined by a distance between an outer surface and inner surface of the model, wherein the at least one area of the model has a density that different than a density of a remaining area of the model, and, as a function of a varying of the default uniform density, a structural configuration of the at least one area of the model includes a plurality of repeating structural elements that are spaced apart from each other by a distance, each repeating structural element extending from the inner surface to the outer surface of the model; and
        convert the modified model into machine readable instructions based on a language for manufacturing the flexible inner line by a 3D printer.

11. The computing system of claim 10, wherein the structural configuration is modified as a function of the varying.

12. The computing system of claim 11, wherein the structural configuration is modified by varying a number of the plurality of repeating structural elements extending between the inner surface and the outer surface of the flexible inner liner.

* * * * *